United States Patent [19]

Futami et al.

[11] Patent Number: 4,740,245

[45] Date of Patent: Apr. 26, 1988

[54] THERMOPLASTIC DENTAL FILLING COMPOSITION

[75] Inventors: Shunichi Futami, Nagareyama; Satoshi Terauchi, Urawa, both of Japan

[73] Assignee: G-C Dental Industrial Corp., Tokyo, Japan

[21] Appl. No.: 898,711

[22] Filed: Aug. 21, 1986

[30] Foreign Application Priority Data

Sep. 12, 1985 [JP] Japan ................................ 60-200594

[51] Int. Cl.[4] ................................................. C09K 3/00
[52] U.S. Cl. ...................................... 106/35; 523/115; 523/116; 433/217.1; 433/228.1
[58] Field of Search ...................... 433/199, 217.1, 226, 433/228.1; 106/35; 523/115, 116, 118, 109

[56] References Cited

U.S. PATENT DOCUMENTS 4,600,389 7/1986 Schwantz ............................ 106/35
4,672,081 7/1987 Fisher et al. ......................... 106/35
4,698,376 10/1987 Asmussen et al. .................. 523/115

*Primary Examiner*—Josephine Barr
*Attorney, Agent, or Firm*—Oblon, Fisher, Spivak, McClelland & Maier

[57] ABSTRACT

A thermoplastic dental filling composition is disclosed, comprising a polymer component containing trans-1,4-polyisoprene and an ethylene/vinyl acetate copolymer resin and an insoluble or sparingly soluble inorganic filler. The filling composition of the invention has similar softening operation properties to natural guttapercha and has a high tensile strength and, therefore, it can be suitably used as a root canal filling material. Further, a composition comprising the above-described dental filling composition having a wax-like component added thereto is used as a temporary filling material.

21 Claims, No Drawings

THERMOPLASTIC DENTAL FILLING COMPOSITION

FIELD OF THE INVENTION

The present invention relates to a composition used in thermoplastic dental filling, which can suitably be applied as root canal filling materials in the dentistry and temporary filling materials for deficient portions of a tooth and used in other medical operations in relation with restoration of teeth.

BACKGROUND OF THE INVENTION

Root canal filling materials are an essential material in the endodontics and after thoroughly removing off staining substances in a root canal, they are filled in the root canal. A typical example of such root canal filling materials is a generally called guttapercha point having such a shape that it is fit to the shape of the root canal and that it is provided at the end terminal thereof with a taper shape so as to make the filling easy. The guttapercha point includes the following two types: a master point (main point) type and an accessory point type.

The master point type is formed in accordance with the international standard and is applied for the filling in a main portion of the root canal which has been reamed by means of a root canal reamer having the same dimension defined in the international standard, such as a reamer, a K-file, and an H-file.

Since the root canal shape is circular in the vicinity of a root apex which has been reamed but non-circular in many of other portions thereof, the accessory point is used in a lateral condensation method by which it is filled in a void portion formed after filling the master point, to make it free from any dead space. Properties necessary for the root canal filling point are that it is appropriately flexible, is tough, and is compressible. Further, it is required to have properties that it has a good adhesion to the root canal wall and can be burnt out or removed by a heat cutter.

In addition, a temporary filling material is filled under pressure in a deficient portion of the tooth upon heating and softening and is supplied in the form of a rod or a pellet. Further, the temporary filling material is used for temporary filling before a permanent filling material has been filled, and when a dental pulp damage is large, it is used for filling until the damage has been completely recovered such that the permanent filling material can be filled. During this period of time, the temporary filling material completely protects a dental cavity and does not cause any change in the position relation of neighbour teeth or opposing teeth. Necessary properties as the temporaty filling material are that it is free from irritation, toxicity, and harms to other properties, does not have solubility and is appropriately tough and resistant to abrasion. Further, it is required that it flows upon softening and pressure contacting and well adheres to the dental cavity and that it can be readily removed after it has been used.

Hitherto, in order to meet the foregoing requirements, guttapercha which is collected from a tree of the sapodilla family living in the tropics and zinc oxide have been used as main components in the dentistry. These components are formed in the form of a narrow point provided with a taper shape and then filled in the root canal so as to fit to the dimension of a reamed root canal. Alternatively, after adjusting the softening operation property by the addition of a wax and other additives to the guttapercha and zinc oxide, the mixture is formed in the form of a rod or a pellet to apply the temporary filling of a dental deficient portion.

However, since guttapercha collected from a tree has a low tensile strength and is too soft, when the resulting filling material is used as a root canal filling point, it is weak, i.e., it has a small deforming stress and in particular, a narrow point is immediately bent, whereby it is especially difficult to fill it into a curved narrow root canal. Further, when it is exposed to direct rays of the sun or in air for from several months to several years, the rubbery properties of the guttapercha are deteriorated, and the point becomes brittle, whereby it is likely to be broken or it causes a blooming phenomenon by which a power generates on a surface thereof.

Further, in the case that large amounts of a wax and other additives are blended for the temporary filling, when stored over several years, the was blended is separated to cause a phenomenon that it sticks to fingers, whereby the operation becomes difficult. Still further, it causes a poor softening property and becomes so brittle that it is likely broken, whereby the material is no longer practically usefull.

In view of the above, so far as natural guttapercha is used, scattering in the quality of the raw material is great, and it is quite difficult to keep a stable quality.

Moreover, there are cases that the material is placed in various circumstances concerning the temperature are humidity after the production and then provided to the dentist for the dental treatment (there may be even a case that it is used for the dental treatment after a lapse of time of several years) and, therefore, among the products, there are ones that cannot be suited for the use. Thus, various claims for clients have been generated.

The natural guttapercha contains trans-1,4-polyisoprene as a main component but is incorporated with foreign components such as other natural resins and impurities. These foreign components are varied depending upon the place of production, and there formulations have not yet been completely clarified. Accordingly, it is impossible to get the starting material of a stable quality, and so far as the natural guttapercha is used as a main component for the dental filling, such problems as those described above are inevitable.

The guttapercha is never domestically yielded in Japan and, therefore, its availability relies on the importation. However, the availability of the guttapercha tends to be affected by the state of affairs in Southeast Asia as the place of production and, therefore, not only its price is considerably expensive, but also a variation in quality is quite vigorous. Thus, a stable supply of guttapercha is for the moment rather difficult.

SUMMARY OF THE INVENTION

The present inventor paid an attention to trans-1,4-polyisoprene as a main component of guttapercha and found that a combination of trans-1,4-polyisoprene which is synthesized for the purpose of supplying a dental filling material having an excellent filling operation with an ethylene/vinyl acetate copolymer resin provides a dental filling material having a softening operation property similar to that in natural guttapercha and having a high tensile strength.

Further, the inventor found that a composition of trans-1,4-polyisoprene and an ethylene/vinyl acetate copolymer resin having added thereto an insoluble or sparingly soluble inorganic filler can produce toughness and be used as a root canal filling material and that the above-described composition can also be used as a temporary filling material by further adding thereto a thermoplastic resin as a modifier and optionally a wax-like component as a softening controller.

These findings have achieved the present invention. Therefore, a primary object of the present invention is to provide a root canal filling material in the dentistry, which is a thermoplastic dental filling composition comprising from 3 to 50% by weight of a polymer component comprising trans-1,4-polyisoprene and an ethylene/vinyl acetate copolymer resin and from 50 to 97% by weight of an insoluble or sparingly soluble inorganic filler.

Another object of the present invention is to a temporary filling material for deficient portion of tooth, which is a thermoplastic dental filling composition comprising from 3 to 50% by weight of an organic component comprising (a) a polymer component comprising trans-1,4-polyisoprene and an ethylene/vinyl acetate copolymer resin and (b) at least one wax-like component having a melting point of 70° C. or less; and from 50 to 97% by weight of an insoluble or sparingly soluble inorganic filler.

DETAILED DESCRIPTION OF THE INVENTION

The trans-1,4-polyisoprene which is used in the present invention is a polyisoprene represented by the following formula:

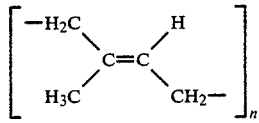

which is different in molecular structure from cis-1,4-polyisoprene represented by the following formula:

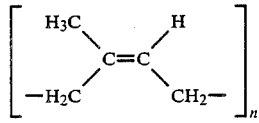

In the present invention, in order to impart softening characteristics and elasticity and to improve compatibility, processability and fluidity in the heat fusion for the purposes of giving properties similar to those of guttapercha, it is an essential condition to combine the trans-1,4-polyisoprene with an ethylene/vinyl acetate copolymer resin.

Properties of an ethylene/vinyl acetate copolymer resin are generally determined by the content of vinyl acetate and melt index (MI). Those ethylene/vinyl acetate copolymer resins having a content of vinyl acetate of less than 15% by weight are not suitable because they are high in rigidity and fail in compatibility with waxes and resins. On the other hand, those ethylene/vinyl acetate copolymer resins having a content of vinyl acetate exceeding 40% by weight are not suitable either, because they are excessively flexible, are great in deformation at room temperatures up to 37° C., and are so tacky that they are likely to adhere to fingers and instruments during the softening operation, leading to difficulty in handling. Accordingly, those having a content of vinyl acetate from 15 to 40% by weight are suitable for use in the present invention.

When the melt index of the ethylene/vinyl acetate copolymer resin is less than 10, the resin is high in softening temperature, is excessively high in toughness, is poor in processibility, and because of its resistance at the softening, it is difficult in softening operation and, hence, such a resin is not suitable for use. The higher the melt index, the more excellent the softening operation properties. In ethylene/vinyl acetate copolymer resins which are commercially available in present, the maximum melt index is 400 and, therefore, the melt index of the ethylene/vinyl acetate copolymer resin which is suitable for use in the present invention is substantially from 10 to 400.

As described above, it is an essential condition in the present invention to use trans-1,4-polyisoprene in combination with an ethylene/vinyl acetate copolymer resin, but such a combined use is made to impart suitable characteristics in quality for the dental filling. That is, the trans-1,4-polyisoprene is used as a base material, whereas the ethylene/vinyl acetate copolymer resin contributes to a reduction of the softening temperature and an improvement of the flexibility. If the ethylene/vinyl acetate copolymer resin is used in an amount exceeding 100 parts by weight bases on 100 parts by weight of the trans-1,4-polyisoprene, a decrease in strength of the resulting material is remarkable. On the other hand, if the ethylene/vinyl acetate copolymer resin is used in an amount of less than 5 parts by weight based on 100 parts by weight of the trans-1,4-polyisoprene, the resulting material is so high in softening temperature in the dental filling that it exhibits a rigid tendency and is difficult in the filling operation, whereby it fails in adhesion to dental cavities. Accordingly, a suitable amount of the ethylene/vinyl acetate copolymer resin is from 5 to 100 parts by weight based on 100 parts by weight of the trans-1,4-polyisoprene.

The thermoplastic dental filling composition is incorporated with an inorganic filler for the purposes of ensuring the X-ray opaque, imparting the rigidity, and reducing the production cost. The inorganic filler which can be used for these purposes is a sparingly soluble or insoluble powder having a solubility of 0.5 g or less in 100 ml of water at 20° C. Suitable examples of the inorganic filler which can be used include silicon compounds such as white carbon; alkaline earth metal surfates such as barium sulfate and calcium sulfate; alkaline earth metal carbonates such as calcium carbonate, basic magnesium arbonate etc.; polyvalent metal silicates such as aluminium silicate, zinc silicate, calcium silicate, magnesium silicate, and zirconium siicate; polyvalent metal oxides such as strontium oxide, magnesium oxide, calcium oxide, zinc oxide, aluminium oxide, titanium oxide, zirconium oxide, and silica; polyvalent metal hydroxides such as magnesium hydroxide, strontium hydroxide, calcium hydroxide, zinc hydroxide, aluminium hydroxide, and zirconium hydroxide; clay minerals such as kaolin, talc, mica, pyrophyllite, montmorillonite, and sericite; and lithopone consisting of barium sulfate and zinc sulfide.

It is clear that the rigidity is increased with an increase in the amount of the filler in the thermoplastic dental filling composition. If the amount of the filler used is less than 50% by weight, not only the flexibility excessively appears and the rigidity is lowered, which results in difficulty in the filling into a dental cavity, but also the X-ray image is so unclear that one cannot definately identify the filling state of the thermoplastic dental filling composition filled in the dental cavity. Accordingly, a minimum amount of the filler is inevitably 50% by weight.

Furthermore, in order that the thermoplastic dental filling composition of the present invention has suitable softening characteristics in the filling operation and exhibits an effect as a binder, the total amount of the trans-1,4-polyisoprene and the ethylene/vinyl acetate copolymer resin is at least 3% by weight, and the amount of the filler is 97% by weight at maximum. That is, suitable amount of an insoluble or sparingly soluble fine powder which can be used as the filler is from 50 to 97% by weight.

A thermoplastic resin is suitably added for the purposes of improving the adhesion to a cavity wall, making the softening operation easy, and improving the softening fluidity. Suitable examples of the thermoplastic resin which can be used for these purposes include polystyrene, styrene-based copolymer resin, low molecular weight polyethylene, low molecular weight polypropylene, olefin-based resin, rosin-based resin, terpene-based resin, alicyclic saturated hydrocarbon resin, and coumarone resin.

In order that the thermoplastic dental filling composition is filled into a dental cavity to achieve a hardened body which is less in deformation, the softening point of the thermoplastic resin as a softening modifier is suitably 60° C. or higher. Further, in order to improve the adhesion to the cavity wall and the softening fluidity, the softening point of the thermoplastic resin is 110° C. or lower. That is, the softening point of the thermoplastic resin which can be used as a softening modifier is restricted to the range of from 60° C. to 110° C.

If the thermoplastic resin which is used for the purpose of improving the softening modification is added in an amount of exceeding 8% by weight with respect to the thermoplastic dental filling composition, the resulting material is brittle and markedly low in flexibility. Accordingly, in the case that minute filling into the dental cavity is required or in the case of the temporary filling, the thermoplastic resin is added in a proportion of not exceeding 8% by weight with respect to the thermoplastic dental filling composition.

In the case that the thermoplastic dental filling composition is used as a temporary filling material in a cavity, in order to increase the fluidity in the softening to improve the adhesion to the cavity and improve the softening operation properties, a wax-like component which can be used as a softening controller is a wax having a melting point of from 37° to 70° C. Examples include waxes such as paraffin wax, microcrystalline wax, white Japan wax, and beeswax; higher fatty acids such as lauric acid, myristic acid, palmitic acid, margaric acid, and stearic acid; and higher alcohols such as myristy alcohol, pentadecanol-1, cetyl alcohol, hexadecanol-2, heptadecanol-1, heptadecanol-2, stearyl alcohol, octadecanol-2, nonadecanol-1, nonadecanol-2, arachyl alcohol eicosanol-2, henecosanol, and behenyl alcohol. If a wax-like component having a melting point of lower than 37° C. is added, the resulting material is soft even at room temperature and so tacky that it adheres to fingers to thereby make the operation difficult, and the deformation of the filled material is large. On the other hand, if a wax-like component having a melting point exceeding 70° C. is added, the hardening goes fast to make the softening operation difficult. Further, if the wax-like component is added in an amount exceeding 20% by weight, the resulting thermoplastic dental filling composition is markedly low in strength and so tacky that it adheres to fingers and filling instruments, whereby it is no longer practically useful. Accordingly, with respect to the wax-like component which is used, a suitable melting point thereof is from 37° C. to 70° C., and a suitable amount thereof is 20% by weight or less with respect to the thermoplastic dental filling composition.

Depending upon cases and purposes of use, the thermoplastic dental filling composition of the present invention can be incorporated with coloring agent, solvent, fungicide, and medicine.

The thermoplastic dental filling composition of the present invention has the following characteristics:

(a) It is tasteless, odorless, non-toxic, and safety;

(b) It is easy to proceeding the softening operation; and (c) It is quite excellent in storage stability.

Thus, the thermoplastic dental filling composition of the present invention is a quite useful material for the dental treatment in the use for root canal filling and temporary filling.

The characteristics of the thermoplastic dental filling composition of the present invention are explained below in more detail.

(1) A thermoplastic dental filling composition according to the present invention comprising a polymer component comprising trans-1,4-polyisoprene and an ethylene/vinyl acetate copolymer resin and an inorganic filler has a deforming stress of approximately twice of that in the conventional product and has a high tensile strength and, therefore, it is a suitable material as a dental root canal filling point.

(2) A composition comprising an organic component containing a polymer component comprising trans-1,4-polyisoprene and an ethylene/vinyl acetate copolymer resin as well as a thermoplastic resin and an inorganic filler has a deforming stress of approximately 1.5 times that in the conventional product and has a high tensile strength. Further, this composition is improved in softening fluidity as compared with the composition as in (1) above and can be readily processed. Thus, it can be suitably used as a material for minute point filling.

(3) By adding a wax-like component as a softening controller to a composition comprising trans-1,4-polyisoprene, an ethylene/vinyl acetate copolymer resin, and an inorganic filler, the fluidity in the softening is increased, the softening temperature is reduced, the adhesion to a cavity wall is improved, and the softening operation by fingers is easy. Thus, it can be suitably used as a temporary filling material.

(4) A composition comprising trans-1,4-polyisoprene, an ethylene/vinyl acetate copolymer resin, and a thermoplastic resin, having added thereto a wax-like component as a softening controller, has a softening resistance lower than that in the case of (3) above and is suitable for the softening operation by fingers. Further, a hardened product resulted therefrom is improved in rigidity and, therefore, the composition can be suitably used as a material for temporary filling which is excellent in durability in an oral cavity.

The present invention is described in more detail with reference to the following examples, but it is not to be construed that the invention is limited thereto.

In the following examples, Examples 1 and 2 are concerned with the use for root canal filling and Examples 3 and 4 with the use for temporary filling, respectively.

EXAMPLE 1

25% by weight of trans-1,4-polyisoprene (TP-301, a trade name of Kuraray Isoprene Chemical Co., Ltd.), 10% by weight of an ethylene/vinyl acetate copolymer resin (Evaflex #250, a trade name of Mitsui Polychemical Co., Ltd.), and 65% by weight of zirconium silicate were charged into a kneader, and the mixture was softened under heating at from 110° to 130° C. and kneaded for 20 minutes, followed by molding into a root canal filling point. This molded article exhibited a high strength and an appropriate flexibility such that the tensile strength was 3.8 kg/mm$^2$ which is approximately twice of that in Comparative Example 1 as described hereinafter and the deforming stress was 130 g which is approximately 1.7 times that in Comparative Example 1. The molded article was evaluated for storage stability by exposing to sunlight for 4 months. As a result, there was observed no change of properties by aging.

EXAMPLE 2

10% by weight of trans-1,4-polyisoprene (TP-301, a trade name of Kuraray Isoprene Chemical Co., Ltd.), 8% by weight of an ethylene/vinyl acetate copolymer resin (Evaflex #310, a trade name of Mitsui Petrochemical Co., Ltd.), 6% by weight of low-molecular weight polystyrene (Piccolastic A-75, a trade name of Rika Hercules Co., Ltd.), and 76% by weight of calcium carbonate were charged into a kneader, and the mixture was heated at from 100° to 120° C. and kneaded for 30 minutes, followed by molding into a root canal filling point. This molded article exhibited a high strength and an appropriate flexibility such that the tensile strength was 3.2 kg/mm$^2$ which is approximately 1.6 times that in Comparative Example 1 and approximately 0.9 time that in Example 1 and that the deforming stress was 195 g which is approximately 2.6 times that in Comparative Example 1 and approximately 1.5 times that in Example 1. The molded article was evaluated for storage stability by exposing to sunlight for 4 months. As a result, there was observed no change of properties by aging.

COMPARATIVE EXAMPLE 1

25% by weight of guttapercha and 75% by weight of zinc oxide were charged into a kneader, and the mixture was heated at from 100° to 120° C. and kneaded for 30 minutes, followed by molding a root canal filling point. This molded article was so soft that the tensile strength was 2.0 kg/mm$^2$ and had a low deforming stress so that it was readily bent. As the result of evaluation for storage stability by exposing to sunlight for 2 months, the resulting molded article became rigid and brittle and showed a change of properties.

The test results of the thermoplastic dental filling compositions in the use for root canal filling are shown in Table 1.

TABLE 1

| Test Item | Example 1 | Example 2 | Comparative Example 1 |
|---|---|---|---|
| Tensile Strength (kg/mm$^2$) | 3.8 | 3.2 | 2.0 |
| Deforming Stress (g) | 130 | 195 | 75 |
| Storage Test (Exposure to Sunlight) | | | |
| after 1 month | O | O | O |

TABLE 1-continued

| Test Item | Example 1 | Example 2 | Comparative Example 1 |
|---|---|---|---|
| after 2 months | O | O | Δ |
| after 3 months | O | O | X |
| after 4 months | O | O | X |

Test condition: measured at room temperature (23±1° C.)
Criteria on storage test:
0: No change was observed and, therefore, the test sample was good.
Δ: The test sample was somewhat rigid.
X: The test sample was brittle and broken.
Deforming stress:
Using a rheometer, the point was placed vertically on a glass sheet, and the maximum resistance value (g) at which the point was bent was measured.

EXAMPLE 3

4% by weight of trans-1,4-polyisoprene (TP-301, a trade name of Kuraray Isoprene Chemical Co., Ltd.), 2% by weight of an ethylene/vinyl acetate copolymer (Evaflex #210, a trade name of Mitsui Polychemical Co., Ltd.), 84% by weight of titanium oxide, 4% by weight of microcrystalline wax, and 6% by weight of paraffin wax were charged into a kneader, and the mixture was softened under heating at from 90° to 100° C. and kneaded for 30 minutes, followed by molding into a rod for temporary filling. This molded article exhibited a tensile strength of 26 kg/cm$^2$ which is approximately 1.7 times that in Comparative Example 2 as described hereinafter and a degree of diminution in size under pressure of 0.5%, 1.8%, 35.9%, and 83.0% at 37° C., 45° C., 50° C., and 55° C., respectively, a tendency of which was similar to that in Comparative Example 2. The molded article was found to be suited for the softening operation.

The molded article was stored in a thermostatic chamber at 60° C. for 2 months. As a result, the molded article had a good softening operation feeling and exhibited a tensile strength of 24 kg/cm$^2$ and a degree of diminution in size under pressure of 0.5%, 1.8%, 34.4%, and 81.3% at 37° C., 45° C., 50° C., and 55° C., respectively. Thus, there was not found a substantial difference in properties from the molded article at the initial stage.

EXAMPLE 4

5% by weight of trans-1,4-polyisoprene (TP-251, a trade name of Kuraray Isoprene Chemical Co., Ltd.), 3% by weight of an ethylene/vinyl acetate copolymer resin (Evaflex #220, a trade name of Mitsui Polychemical Co., Ltd.), 2% by weight of rosin, 50% by weight of kaolin, 29% by weight of barium sulfate, 6% by weight of cetyl alcohol, and 5% by weight of white Japan wax were charged into a kneader, and the mixture was softened under heating at from 90° to 110° C. and kneaded for 30 minutes, followed by molding into a rod for temporary filling. This molding article exhibited a tensile strength of 24 kg/cm$^2$ which is slightly lower than that in Example 3 but is approximately 1.6 times that in Comparative Example 2 and a degree of diminution in size under pressure of 0.6%, 1.8%, 67.7%, and 85.6% at 37° C., 45° C., 50° C., and 55° C., respectively, i.e., it was especially high in degree of diminution in size under pressure at 50° C. as compared with those in Example 3 and Comparative Example 2 and, hence, a softening operation allowance was thoroughly ensured. The molded article was found to be suited for the softening operation.

The molded article was stored in a thermostatic chamber at 60° C. for 2 months. As a result, the molded article had a good softening operation feeling and exhibited a tensile strength of 24 kg/cm² and a degree of diminution in size under pressure of 0.5%, 1.7%, 66.2%, and 85.0% at 37° C., 45° C., 50° C., and 55° C., respectively. Thus, there was not found a substantial difference in properties from the molded article at the initial stage.

COMPARATIVE EXAMPLE 2

12% by weight of guttapercha, 8% by weight of calcium hydroxide, 70% by weight of calcium silicate, 8% by weight of paraffin wax, and 2% by weight of beeswax were charged into a kneader, and the mixture was heated at from 90° to 110° C. and kneaded for 30 minutes, followed by molding into a rod for the temporary filling (diameter: 4 mm, length: 9 cm). This molded article exhibited a tensile strength of 15 kg/cm² and a degree of diminution in size under pressure of 0.5%, 2.0%, 45.4%, and 85.7% at 37° C., 45° C., 50° C., and 55° C., respectively. The molded article was found to be suited for the softening operation.

The molded article was stored in a thermostatic chamber at 60° C. for 2 months. As a result, the tensile strength was lowered to about one fourth, i.e., 4 kg/cm², and the degree of diminution in size under pressure at 50° C. and 55° C. was lowered to 15.0% and 28.0%, respectively, i.e., the softening fluidity under pressure was lowered to one third. Further, the molded article was felt hot in the softening operation, and separation of the waxes was observed.

The test results of the thermoplastic dental filling compositions for the temporary filling are shown in Table 2.

TABLE 2

| Test Item | Example 3 | Example 4 | Comparative Example 2 |
|---|---|---|---|
| [Before Storage] | | | |
| Softening Operation | good | good | good |
| Tensile Strength (kg/cm²) | 26 | 24 | 15 |
| Degree of Diminution in Size under Pressure (%) | | | |
| at 37° C. | 0.5 | 0.6 | 0.5 |
| at 45° C. | 1.8 | 1.8 | 2.0 |
| at 50° C. | 35.9 | 67.7 | 45.4 |
| at 55° C. | 83.0 | 85.6 | 85.7 |
| [After Forced Storage 60° C. for 2 Months] | | | |
| Appearance | good (No change was observed.) | good (No change was observed.) | Separation of the waxes was observed. |
| Softening Operation | good | good | It was felt hot. |
| Tensile Strength (kg/cm²) | 24 | 23 | 4 |
| Degree of Diminution in Size under Pressure (%) | | | |
| at 37° C. | 0.5 | 0.5 | 0.8 |
| at 45° C. | 1.8 | 1.7 | 2.1 |
| at 50° C. | 34.4 | 66.2 | 15.8 |
| at 55° C. | 81.3 | 85.0 | 28.0 |

Test condition: measured at 23±1° C.

Degree of diminution in size under pressure: according to JIS T-6507

Tensile strength: A sample having a diameter of 4.6 mm and a length of 50 mm was prepared, and measurement was carried out using an autograph made by Shimazu Seisakusho Ltd.

It is evident from the foregoing results that the thermoplastic dental filling composition according to the present invention is, in particular, substantially free from deterioration after the forced storage and can keep a stable quality. Further, it can be advantageously applied to even narrow and complicated root canals in the use of root canal filling because it has a high tensile strength and is tough. Still further, since the composition of the present invention with regard to the use of temporary filling has a tensile strength of approximately 1.6 times that in Comparative Example 2, is less in deformation, and is free from a fair of falling, it is advantageous in filling a dental cavity.

Accordingly, the thermoplastic dental filling composition according to the present invention can give rise to marked improvements for not only root canal filling but also temporary filling.

While the invention has been described in detail and with reference to specific embodiments thereof, it will be apparent to one skilled in the art that various changes and modifications can be made therein without departing from the spirit and scope thereof.

What is claimed is:

1. A thermoplastic dental filling composition comprising from 3 to 50% by weight of a polymer component comprising trans-1,4-polyisoprene and an ethylene/vinyl acetate copolymer resin, said copolymer resin comprising from 15 to 40 wt. % vinyl acetate and having a melt index substantially from 10 to 400, and from 50 to 97% by weight of an insoluble or sparingly soluble inorganic filler, said filler having a solubility of 0.5 g or less in 100 ml water at 20° C.

2. A thermoplastic dental filling composition as claimed in claim 1, wherein the amount of said ethylene/vinyl acetate copolymer resin in said polymer component is from 5 to 100 parts by weight based on 100 parts by weight of said trans-1,4-polyisoprene.

3. A thermoplastic dental filling composition as claimed in claim 1, wherein said inorganic filler is selected from the group consisting of a silicon compound, an alkaline earth metal sulfate, an alkaline earth metal carbonate, a polyvalent metal silicate, a polyvalent metal oxide, a polyvalent metal hydroxide, a clay mineral, and lithopone.

4. A thermosplastic dental filling composition comprising from 3 to 50% by weight of an organic component comprising (a) a polymer component comprising trans-1,4-polyisoprene and an ethylene/vinyl acetate copolymer resin, said copolymer resin comprising from 15 to 40 wt. % vinyl acetate and having a melt index substantially from 10 to 400, and (b) at least one thermoplastic resin selected from the group consisting of polystyrene, a styrene-based copolymer resin, low molecular weight polyethylene, low molecular weight polypropylene, an olefin-based resin, a rosin-based resin, a terpene-based resin, an alicyclic saturated hydrocarbon resin, and a coumarone resin; and from 50 to 97% by weight of an insoluble or sparingly soluble inorganic filler, said filler having a solubility of 0.5 g or less in 100 ml water at 20° C.

5. A thermoplastic dental filling composition as claimed in claim 4, wherein the amount of said ethylene/vinyl acetate copolymer resin in said polymer component is from 5 to 100 parts by weight based on 100 parts by weight of said trans-1,4-polyisoprene.

6. A thermoplastic dental filling composition as claimed in claim 4, wherein said inorganic filler is selected from the group consisting of a silicon compound, an alkaline earth metal sulfate, an alkaline earth metal carbonate, a polyvalent metal silicate, a polyvalent metal oxide, a polyvalent metal hydroxide, a clay mineral, and lithopone.

7. A thermoplastic dental filling composition as claimed in claim 4, wherein said thermoplastic resin has a softening point of from 60° to 110° C.

8. A thermoplastic dental filling composition as claimed in claim 4, wherein said thermoplastic resin is added in an amount of up to 8% by weight with respect to said thermoplastic dental filling composition.

9. A thermoplastic dental filling composition comprising from 3 to 50% by weight of an organic component comprising (a) a polymer component comprising trans-1,4-polyisoprene and an ethylene/vinyl acetate copolymer resin, said copolymer resin comprising from 15 to 40 wt. % vinyl acetate and having a melt index substantially from 10 to 400, and (b) at least one wax-like component having a melting point of 70° C. or less, selected from the group consisting of a natural wax, a synthetic wax, a higher fatty acid, and a higher alcohol; and from 50 to 97% by weight of an insoluble or sparingly soluble inorganic filler, said filler having a solubility of 0.5 g or less in 100 ml water at 20° C.

10. A thermoplastic dental filling composition as claimed in claim 9, wherein the amount of said ethylene/vinyl acetate copolymer resin in said polymer component is from 5 to 100 parts by weight based on 100 parts by weight of said trans-1,4-polyisoprene.

11. A thermoplastic dental filling composition as claimed in claim 9, wherein said inorganic filler has a solubility of 0.5 g or less in 100 ml of water at 20° C.

12. A thermoplastic dental filling composition as claimed in claim 9, wherein said inorganic filler is selected from the group consisting of a silicon compound, an alkaline earth metal sulfate, an alkaline earth metal carbonate, a polyvalent metal silicate, a polyvalent metal oxide, a polyvalent metal hydroxide, a clay mineral, and lithopone.

13. A thermoplastic dental filling composition as claimed in claim 9, wherein said wax-like component has a melting point of from 37° to 70° C.

14. A thermoplastic dental filling composition as claimed in claim 9, wherein said wax-like component is added in an amount of up to 20% by weight with respect to said thermoplastic dental filling composition.

15. A thermoplastic dental filling composition comprising from 3 to 50% by weight of an organic component comprising (a) a polymer component comprising trans-1,4-polyisoprene and an ethylene/vinyl acetate copolymer resin, said copolymer resin comprising from 15 to 40 wt. % vinyl acetate and having a melt index substantially from 10 to 400, (b) at least one thermoplastic resin selected from the group consisting of polystyrene, a styrene-based copolymer resin, low molecular weight polyethylene, low molecular weight polypropylene, an olefin-based resin, a rosin-based resin, a terpene-based resin, an alicyclic saturated hydrocarbon resin, and a coumarone resin, and (c) at least one wax-like component having a melting point of 70° C. or less, selected from the group consisting of a natural wax, a synthetic wax, a higher fatty acid, and a higher alcohol; and from 50 to 97% by weight of an insoluble or sparingly souble inorganic filler, said filler having a solubility of 0.5 g or less in 100 ml water at 20° C.

16. A thermoplastic dental filling composition as claimed in claim 15, wherein the amount of said ethylene/vinyl acetate copolymer resin in said polymer component is from 5 to 100 parts by weight based on 100 parts by weight of said trans-1,4-polyisoprene.

17. A thermoplastic dental filling composition as claimed in claim 15, wherein said inorganic filler is selected from the group consisting of a silicon compound, an alkaline earth metal sulfate, as alkaline earth metal carbonate, a polyvalent metal silicate, a polyvalent metal oxide, a polyvalent metal hydroxide, a clay mineral, and lithopone.

18. A thermoplastic dental filling composition as claimed in claim 15, wherein said thermoplastic resin has a softening point of from 60° to 110° C.

19. A thermoplastic dental filling composition as claimed in claim 15, wherein said thermoplastic resin is added in an amount of up to 8% by weight with respect to said thermoplastic dental filling composition.

20. A thermoplastic dental filling composition as claimed in claim 15, wherein said wax-like component has a melting point of from 37° to 70° C.

21. A thermoplastic dental filling composition as claimed in claim 15, wherein said wax-like component is added in an amount of up to 20% by weight with respect to said thermoplastic dental filling composition.

* * * * *